US012805824B2

(12) United States Patent
Hofmann et al.

(10) Patent No.: US 12,805,824 B2
(45) Date of Patent: Nov. 24, 2026

(54) REDUCING AN X-RAY DOSE APPLIED ON A SUBJECT DURING A RESPIRATION-CORRELATED COMPUTED TOMOGRAPHY SCAN

(71) Applicant: Siemens Healthineers AG, Forchheim (DE)

(72) Inventors: Christian Hofmann, Erlangen (DE); Marc Vornehm, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 149 days.

(21) Appl. No.: 18/816,468

(22) Filed: Aug. 27, 2024

(65) Prior Publication Data

US 2025/0072858 A1 Mar. 6, 2025

(30) Foreign Application Priority Data

Sep. 4, 2023 (EP) .................................... 23195100

(51) Int. Cl.

| | |
|---|---|
| ***A61B 6/00*** | (2024.01) |
| ***A61B 6/03*** | (2006.01) |
| ***A61B 6/50*** | (2024.01) |

(52) U.S. Cl.

CPC ................ *A61B 6/542* (2013.01); *A61B 6/03* (2013.01); *A61B 6/50* (2013.01)

(58) Field of Classification Search

None

See application file for complete search history.

(56) References Cited

U.S. PATENT DOCUMENTS

2017/0238895 A1 8/2017 Hofmann
2020/0121266 A1 4/2020 Hofmann

FOREIGN PATENT DOCUMENTS

DE 102011079496 A1 * 1/2013 ............ A61B 6/032

OTHER PUBLICATIONS

Werner Rene et al. "intelligent 4D CT sequence scanning (i4DCT): First scanner prototype implementation and phantom measurements of automated breathing signal guided 4D CT" med. Phy. 47(6), Jun. 2020, pp. 2408-2412 (Year: 2020).*

Werner Rene et al;.: "Intelligent 4D CT sequence scanning (i4DCT): First scanner prototype implementation and phantom measurements of automated breathing signal-guided 4D CT", Med.Phys. 47 (6), Jun. 2020, pp. 2408-2412.

* cited by examiner

*Primary Examiner* — Hoon K Song

(74) *Attorney, Agent, or Firm* — Harness, Dickey & Pierce, P.L.C.

(57) ABSTRACT

A computer-implemented method for reducing an X-ray dose applied on a subject during a respiration-correlated computed tomography scan includes determining a beginning of a data-redundant breathing phase during a beam-on period of the scan; applying a redundancy modulation to the applied X-ray dose such that the X-ray dose is reduced during the data-redundant breathing phase; determining an end of the data-redundant breathing phase; and continuing the scan without a redundancy modulation of the X-ray dose at the end of the data-redundant breathing phase.

20 Claims, 4 Drawing Sheets

REDUCING AN X-RAY DOSE APPLIED ON A SUBJECT DURING A RESPIRATION-CORRELATED COMPUTED TOMOGRAPHY SCAN

CROSS-REFERENCE TO RELATED APPLICATION(S)

The present application claims priority under 35 U.S.C. § 119 to European Patent Application No. 23195100.5, filed Sep. 4, 2023, the entire contents of which is incorporated herein by reference.

FIELD

One or more example embodiments relates to a computer-implemented method for reducing an X-ray dose applied on a subject during a respiration-correlated computed tomography scan and a corresponding computer program computer-readable storage medium, and computed tomography system.

Independent of the grammatical term usage, individuals with male, female or other gender identities are included within the term.

RELATED ART

Respiration-correlated computed tomography (CT) imaging, also referred to as four-dimensional (4D) CT imaging, is frequently used as basis for radiotherapy treatment planning. 4D CT imaging is a method for measuring anatomic motion induced by patient respiration. During CT acquisition, respiration of the patient is monitored and set in relation to the initiation time of the CT scan. Accordingly, reconstructed CT slices can be correlated to the breathing phase of the patient's respiratory cycle. By selecting corresponding slices correlated to different phases of the breathing cycle, CT images can be generated at multiple breathing phases.

4D CT image quality has traditionally been severely affected by image artefacts. This originates from the retrospective analysis and correlation of the breathing cycles with the CT scan. For example due to irregularities in a patient's breathing cycle, the acquired data coverage may be insufficient for reconstruction of image slices at particular breathing states. This might even lead to the necessity of repeating the CT scan and thus additional X-ray dose being applied. In order to tackle this problem, it has been proposed to fulfil a data sufficiency condition (DSC). The DSC demands that for each couch position of a desired scan range, projection data have been acquired for at least an entire breathing cycle of the patient. A corresponding method is described by R. Werner, T. Sentker, F. Madesta, T. Gauer, and C. Hofmann in "Intelligent 4D CT sequence scanning (i4DCT): Concept and performance Evaluation", Med. Phys. 46 (8), August 2019, p. 3462-3474. The intelligent 4D CT sequence scanning (i4DCT) is a method for respiration-correlated 4D CT scanning in which the start and end points (beam on and beam off events) of the data acquisition process at a given couch position are triggered by the patient's respiration. Each beam on period covers a full breathing cycle from end-inhalation to end-inhalation to ensure fulfilment of the DSC at each couch position. With this adaption, it can be ensured that all relevant breathing states of a patient's breathing cycle are recorded at each couch position.

SUMMARY

While i4DCT has thus introduced a considerable advantage, it is still desirable to further improve 4D CT imaging. In particular, it would be advantageous to reduce the applied X-ray dose.

One or more example embodiments provides a way to improve 4D CT imaging, preferably to provide a way to reduce an applied X-ray dose.

This is met or exceeded by a method according to claim 1, a computer program according to claim 13, a computer-readable storage medium according to claim 14 and a computed tomography system according to claim 15. Further advantages and features result from the dependent claims, the description and the attached figures.

BRIEF DESCRIPTION OF THE DRAWINGS

The accompanying drawings illustrate various exemplary embodiments and methods of various aspects.

Similar elements are designated with the same reference signs in the drawings. In the drawings.

DETAILED DESCRIPTION

Figure 1:
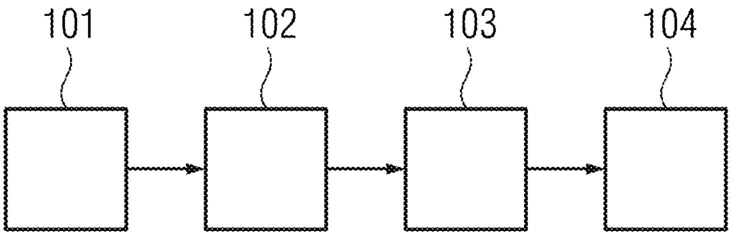
FIG. 1 shows a flow diagram of a method according to an embodiment of the invention.

According to one or more example embodiments, a computer-implemented method for reducing an X-ray dose applied on a subject during a respiration-correlated computed tomography (CT) scan is provided. The method comprises the following steps:

(a) during a beam-on period of the scan, determining the beginning of a data-redundant breathing phase;

(b) during the data-redundant breathing phase, applying a redundancy modulation to the applied X-ray dose such that the X-ray dose is reduced during the data-redundant breathing phase;

(c) determining the end of the data-redundant breathing phase;

(d) at the end of the data-redundant breathing phase, continuing the scan without the redundancy modulation of the X-ray dose.

Advantageously, the X-ray dose applied to the subject may be reduced via this method by taking into account data-redundant breathing phases and modulating the applied X-ray dose accordingly.

A subject may be a human being or an animal. For example, the subject may be a patient. The subject may be a patient that is subjected to radiation therapy, in particular radiation therapy that is monitored via respiration-correlated CT scanning.

The term "X-ray dose" is to be understood broadly in the context of this invention. It generally describes an X-ray radiation dose quantity that is absorbed by and/or sent towards a subject or a part of a subject. Typically, the dose may be absorbed by tissue of the subject. It can be a measure of radiation energy that incident radiation deposits in the subject's tissue. The dose can be measured in the SI unit "gray" (Gy) or in other units, such as the unit "Rad". Both, overall dose (absorbed by the subject in total) as well as a local dose (absorbed by a part of the subject, e.g. a scanned organ), can be relevant. The X-ray dose may be controlled by controlling the output of at least one X-ray source of a CT system. Controlling the X-ray source may, for example, comprise controlling the intensity of emitted X-ray radiation, the direction of the emitted X-ray radiation (in particular relative to the location of the subject), and/or a blocking of a radiation path of emitted X-ray radiation.

A beam-on period of the scan is a period in which at least one X-ray beam is switched on. Typically, during a CT scan, the subject is moved into different couch positions, and CT data are acquired at the different couch positions. The couch position describes the position of the subject in the direction of a CT system's gantry longitudinal axis. The position of the subject is typically adjusted by moving a movable patient table. The couch position may also be referred to as z-position. The time of data acquisition usually corresponds to a beam-on period, i.e. to the time that the X-ray beam used for data acquisition is switched on. Preferably, the beam-on periods of the CT scan may cover a full breathing cycle, respectively. A full breathing cycle may comprise a whole breathing process from one breathing state till the next periodic reoccurrence of the same breathing state. For example, a full breathing cycle may go from end-inhalation to end-inhalation. End-inhalation can be defined to be the breathing state at maximum inhalation, in particular just before the subject starts breathing out again. Preferably, in the context of this invention, a breathing cycle may be considered to begin and end at an end-inhalation state, in particular at two consecutive end-inhalation states.

The respiration-correlated computed tomography scan may be based on covering a full breathing cycle at each couch position. Preferably the breathing cycle may be covered from end-inhalation to end-inhalation. This can be a particularly suitable point in the breathing cycle to monitor the breathing cycle and adjust the CT scan accordingly. The start and end points (i.e., beam on and beam off events) of the data acquisition process at a given couch position may be triggered by a real-time analysis of the patient's respiration. Preferably, in between consecutive beam-on periods there may be at least one breathing cycle, during which the X-ray beam is switched off. In other words, in between consecutive beam-on periods there may be beam-off periods having a duration of at least one breathing cycle. The respiration-correlated computed tomography scan may in particular be based on intelligent 4D CT sequence scanning (i4DCT).

The term "breathing phase" is to be understood broadly in the context of this invention. It generally describes a phase, i.e. a part, of the breathing cycle. A breathing phase may, for example, be a part of the breathing cycle during which the subject inhales or a part during which the subject exhales or a part during which the subject pauses from both inhaling and exhaling, e.g. between an exhaling phase and an inhaling phase. However, any other kind of breathing phase may be determined as well, e.g. depending on the context.

A data-redundant breathing phase is in particular a breathing phase, during which no additional CT data can be acquired during a breathing cycle and/or at one couch position that contains any additional significant information with respect to data acquired during the rest of the breathing cycle at the current couch position. The beginning and end of the data-redundant breathing phase may be determined by monitoring the breathing of the subject. Determining the beginning and/or the end of the data-redundant breathing phase may be based on a reference breathing cycle. The reference breathing cycle may be specific for the subject that is currently examined by the CT scan. The reference breathing cycle may be determined based on data acquired before the beginning of the CT scan. Additionally or alternatively the reference breathing cycle may be determined based on data acquired during the CT scan. The reference breathing cycle may be updated during the CT scan. The updating may be based on monitoring the breathing of the subject during the scan. Updating the reference breathing cycle may be advantageous to counter drift effects of the monitoring or changes in the subject's breathing pattern. The redundancy modulation may be applied by reducing the X-ray output of at least on X-ray source of the CT system. Additionally and/or alternatively, the redundancy modulation may be applied by changing the direction of the X-ray output of at least on X-ray source of the CT system. Additionally and/or alternatively, the redundancy modulation may be applied by blocking at least part of the X-ray output of at least on X-ray source of the CT system. The term redundancy modulation is generally to be understood broadly in the context of this invention and it is in particular defined to provide a reduction in the applied X-ray dose. Optionally, a reduction of the X-ray dose may comprise a reduction of the X-ray dose to zero or nearly zero.

It has been found by the inventors that for many patients, at least during some cycles, a breathing cycle comprise breathing phases of up to several seconds where no significant respiratory motion takes place. This is typically the case in an end-exhalation state. The inventors have noticed that data acquired during such a breathing pause does not provide significant additional information or only very little additional information. Since respiration-correlated computed tomography aims to observe data for several breathing states (e.g. at maximum inhalation, at minimal inhalation and at breathing states in between these end points), data from such a breathing pause is often not actually needed to monitor all the required breathing states. Accordingly, instead of applying the data sufficiency condition by acquiring an entire breathing cycle at full dose, the X-ray dose can be reduced at redundant parts of the breathing cycle. Modulating the X-ray dose to be reduced can thus advantageously prevent the exposure of the subject to unnecessary ionizing radiation. Hence, the X-ray dose may be reduced when data redundancy allows for it. Thus, the dose may be reduced without significant restrictions to the full phase selectivity of a retrospective 4D CT reconstruction.

According to an embodiment, a breathing phase is determined to be data-redundant when it is estimated to provide no significant additional breathing states during the current breathing cycle and/or at the current couch position. For example, it may be provided that the breathing is determined to be data-redundant when a breathing pause after an exhalation phase is detected.

In the context of this invention, the term "breathing state" is to be understood broadly. It generally may describe any state of the subject's breathing. For example, maximum inhalation or minimum inhalation during a breathing cycle may be examples of breathing states. The breathing state may in particular be correlated or defined by the extension and contraction of the subject's lung. The breathing state may be defined by a surrogate parameter. The surrogate parameter may be related to the subject's breathing state. For example, an elevation of the subject's chest may be used to define the breathing state.

The term "significant additional breathing state" may be understood such that an additional breathing state is very close to at least one already measured breathing state during this breathing cycle and/or at the current couch position. The already measured breathing state may in particular be the previous breathing state. The term "very close" may be defined by a threshold difference. Additionally or alternatively, the term "very close" may be defined by a typical measurement accuracy and/or measurement signal noise.

According to an embodiment, a breathing phase is determined to be data-redundant, when a change of the breathing state over time is estimated to be below a threshold and/or when a variance of the breathing state is estimated to remain within a predetermined range. Advantageously the application of the redundancy modulation may thus start as soon as the breathing state remains essentially constant.

According to an embodiment, a respiratory signal is monitored in order to determine the beginning and end of the data-redundant breathing phase. The respiratory signal may be monitored via a surrogate signal. A surrogate signal may be signal that defines a surrogate parameter. For example, a surrogate signal may be a signal that is correlated to the breathing state of the subject. For example, the surrogate signal may comprise information about an elevation of the subject's chest. Hence, while breathing typically comprises an expansion and contraction of the lungs (i.e., a three-dimensional object and, thus a change in three-dimensional space) an elevation of the chest (a change in one direction) may be still useful to define the breathing state, since, typically there is a correlation between the elevation of the chest and the whole movement of the lungs/chest. The respiratory signal may be monitored by a strain gauge. The strain gauge may be connected to the subject's chest. For example, the strain gauge may at least partially surround the subject's chest. Accordingly, the CT system may comprise a strain gauge configured to determine the subject's breathing state. The strain gauge may comprise a belt or be part of a belt that is configured to be wrapped around the subject's chest. Hence, the respiratory signal may be monitored by a belt that is wrapped around the subject's chest and that comprises a strain gauge. Additionally or alternatively, the respiratory signal may be monitored via at least one light marker, such as an infrared marker, and a corresponding, camera, such as an infrared camera. In the context of this invention, term "light" is to be understood broadly. It may comprise any kind of electromagnetic signal that can be detected. In particular the term light comprises infrared light. The light marker may be configured to emit a light signal, in particular an infrared signal. Alternatively the light marker may comprise a light reflector, in particular an infrared light reflector. The light marker may be placed on the subject's chest. The camera may be placed at the end of the table. The camera may be configured to receive a light signal from the light marker. The computed tomography system may comprise the light marker and/or the camera. Optionally, the computed tomography system may comprise a light emitter that is configured to emit light such that the light is reflected by the light reflector.

In the context of this invention, the respiratory signal may, for example, be denoted as $\zeta_i$, wherein i denotes a point in time. $\zeta_i$ may in particular denote an elevation of the subject's chest. $\zeta_i$ may also be referred to as breathing state or breathing signal at time point i. The derivative of the respiratory signal at time point i may be denoted as $\dot{\zeta}_i$. The derivative of the respiratory signal may also be referred to as the breathing velocity. Based on the monitored respiratory signal, a reference breathing signal $\zeta^{ref}$ may be determined. The reference breathing signal is in particular specific for the subject. Hence, the reference breathing signal may be referred to as subject-specific reference signal. The reference breathing signal may be determined prior to starting the respiration correlated computed tomography scan. The reference breathing signal may be updated based on the respiratory signal monitored during the respiration correlated computed tomography scan. Via the reference breathing signal, a reference breathing cycle may be defined. The reference breathing cycle may be defined analogous to the definition used for generally defining the breathing cycle, e.g. as described herein.

According to an embodiment, a necessary condition for the determination of the beginning of a data-redundant breathing phase is a signal length since the last end-inhalation state having a defined minimum length relative to a reference exhalation duration. Preferably, the condition may be determined to be fulfilled if the condition is or was fulfilled at any point in time during at least one previous or the current respiratory measurement sample during the current breathing cycle. The exhalation duration is in particular the duration from the end-inhalation state to the minimum breathing state or to a breathing state that is above the minimum breathing state by a defined absolute or relative amount. For example, the defined amount may be 5%. The amount may be based on a temporal resolution of the respiration-correlated CT scan. For example, the respiration-correlated CT scan may be configured to take images in steps of a particular percentage of the breathing state amplitude, such as in steps of 5% or 10% of the amplitude. For example, reconstruction bins may be provided that are used to sort CT data based on the breathing states. The reconstruction bins may be defined according to percentage values of the current breathing state relative to the maximum breathing state. For example, one reconstruction bin may be for up 90% to 100%, one for 80% to 90% etc. In the context of this invention, the breathing state amplitude may be seen as the difference between the minimum and the maximum breathing state. Advantageously, the amount may thus be chosen such, that it corresponds to the temporal resolution. The minimum breathing state may be defined to be the breathing state at maximum exhalation. The reference exhalation duration may be based on a subject-specific reference breathing signal and/or an average exhalation duration. Hence, the reference exhalation duration may be the exhalation duration of a reference breathing cycle determined from the reference breathing signal. The average exhalation duration may be determined via the respiration monitoring and by determining the average time that the exhalation duration of the subject takes during the monitoring. Advantageously, the signal length since the last end-inhalation state is thus monitored. Via the condition according to this embodiment it can thus be ensured that the redundancy modulation is not started before a typical exhalation phase of the subject ends. The relation to the reference exhalation may be used to define how sure this condition is with respect to not-missing essential data. The relation may be defined by a pre-factor. The pre-factor may depend on an estimated variance or standard deviation of the subject's exhalation duration. The pre-factor may be pre-set. The pre-factor may be updated dynamically based on the monitored respiratory signal, in particular based on the determined variance or standard deviation. In the context of this invention, the variance or standard deviation is to be understood broadly and encompasses any equivalent measure of data variation. Advantageously, via the pre-factor it may be ensured that the risk of missing essential data can be reduced by adapting the condition accordingly with this pre-factor.

For example, the necessary condition for the determination of the beginning of a data-redundant breathing phase may be defined by the term $$\exists\,\zeta_i:\ \sum_{j=i_{100\%}}^{i} H(\zeta_{j-1}-\zeta_j) \geq 1.1 \times i_{5\%exh}^{ref},$$

or an equivalent term, wherein $i_{100\%}$ is the sample index representing the last state of maximal inhalation (i.e., the beginning of the current breathing cycle), H(x) is the Heaviside step function, $$i_{5\%\ exh}^{ref}$$

is the sample index corresponding to the 5% exhalation state, i.e. 5% above the minimum breathing state, in the reference breathing cycle. 1.1 is a pre-factor as described above. This particular pre-factor of 1.1 may be substituted by any other suitable pre-factor. For example, the 1.1 may be replaced by a more general pre-factor k1 in the above term. The 5% exhalation state may be substituted by any other percentage. Optionally, the percentage may be 0%. For example, the 5% in the above term may generally be replaced by x %, x being a free variable defining a percentage value.

According to an embodiment, a necessary condition for the determination of the beginning of a data-redundant breathing phase is the current breathing cycle having gone through a minimum fraction of a reference breathing amplitude during exhalation since the last end-inhalation state. Preferably, the condition may be determined to be fulfilled if the condition is or was fulfilled at any point in time during at least one previous or the current respiratory measurement sample during the current breathing cycle. The fraction of the reference breathing amplitude may be defined by a scaling factor. The scaling factor may be based on an estimated variance or standard deviation of the subject's breathing amplitude. For example, the subject may occasionally inhale deeper than on average. The setting of the scaling factor may be decided based on an expected drift of the measurement. The scaling factor may be pre-set. The scaling factor may be updated dynamically based on the monitored respiratory signal, in particular based on the determined variance or standard deviation. This condition may help to ensure that the redundancy modulation is not applied before the subject is gone through an essentially complete or at least mostly complete exhalation.

For example, the necessary condition for the determination of the beginning of a data-redundant breathing phase may be defined by the term $$\exists\,\zeta_i:\ \zeta_i \leq \mathrm{median}(\zeta_{100\%}) - 0.8 \times \Delta\zeta^{ref}$$

or an equivalent term, wherein $\mathrm{median}(\zeta_{100\%})$ is the median of all previous samples that represent measurements at end-inhalation, and $\Delta\zeta^{ref}$ is the peak-to-peak amplitude of the reference breathing cycle. 0.8 is a scaling factor as described above. This particular scaling factor of 0.8 may be substituted by any other suitable scaling factor. For example, the 0.8 may be replaced by a more general pre-factor k2 in the above term.

According to an embodiment, a necessary condition for the determination of the beginning of a data-redundant breathing phase is based on the current time-dependent change of the breathing state being low. Preferably, the condition may be determined to be fulfilled if the condition is or was fulfilled at any point in time during at least one previous or the current respiratory measurement sample during the current breathing cycle. Hence, it may be assumed that a low current change of breathing state may indicate the beginning of a data-redundant breathing phase.

According to an embodiment, a phase space is defined by a coordinate system, with a first axis being the breathing state and a second axis being the time-dependent change of the breathing state, wherein a current polar angle of a point in phase space at the current breathing state and the current time-dependent derivative of the breathing state is defined with respect to the centre of mass of a reference breathing cycle in the phase space, wherein a necessary condition for the determination of the beginning of a data-redundant breathing phase is the current polar angle being greater than or equal to a reference angle based on the reference breathing cycle. Preferably, the condition may be determined to be fulfilled if the condition is or was fulfilled at any point in time during at least one previous or the current respiratory measurement sample during the current breathing cycle.

The time-dependent change of the breathing state may also be referred to as the derivative of the breathing state or the breathing velocity. Via this condition, both a breathing velocity can be monitored to be low and the breathing state can be monitored to be low (i.e. close to the minimum) as well. The reference angle is in particular the angle in the reference breathing cycle at a minimum breathing state or at a breathing state that is above the minimum breathing state by a defined absolute or relative amount. The amount may be defined equivalently as the amount for other conditions as described above.

For example, the necessary condition for the determination of the beginning of a data-redundant breathing phase may be defined by the term $$\exists\,\zeta_i:\ \varphi_i \geq \varphi_{5\%exh}^{ref}$$

or an equivalent term, wherein the phase is defined as the polar angle $\varphi_i$ of the point $(\dot{\zeta}_i, \zeta_i)$ with respect to the centre of mass of the reference breathing cycle. Hence, the phase of at least one measurement must have been greater than or equal to the phase at 5% exhalation state in the reference breathing cycle. The 5% exhalation state may be substituted by any other percentage. Optionally, the percentage may be 0%. For example, the 5% in the above term may generally be replaced by y %, y being a free variable defining a percentage value.

Preferably, multiple of the necessary conditions may be applied. Accordingly, the data-redundant breathing phase may be determined to begin only when all of these multiple necessary conditions are fulfilled during one breathing cycle and/or at one couch position.

According to an embodiment, the end of the data-redundant breathing phase is estimated to be reached when the current breathing state exceeds a minimal threshold and/or when a change of the current breathing state exceeds a minimal threshold. For example, an X-ray tube current may be increased again at the end of the data-redundant breathing phase. The minimal threshold may depend on the minimum recorded breathing state of the current breathing cycle. For example, an absolute or relative margin may be added on the minimum recorded breathing state to determine the minimal threshold. According to an embodiment, the end of the data-redundant breathing phase is estimated to be reached when the current breathing state exceeds a defined margin above the minimal breathing state recorded in the current breathing cycle and/or in the current couch position and/or since the last end-inhalation state. For example, the margin may be a percentage value, such as 5%. The margin may be based on a temporal resolution of the respiration-correlated CT scan as explained above with respect to a corresponding amount. The CT system may be configured such that as long as this end condition is fulfilled the beginning of the data-redundant breathing phase may not be triggered. Hence, for example, this may prevent the method to trigger the redundancy modulation at all in some cases, e.g. in cases without a pause at end-exhalation.

According to an embodiment, the X-ray dose is modulated by reducing an X-ray tube current when the redundancy modulation is applied. A reduced x-ray tube current may require a longer acquisition time to achieve a good quality. Accordingly, for parts of the data that are acquired during the redundancy modulation a reconstruction may use data that is acquired over a larger amount of time. In other words, reconstruction bins within this period of redundancy modulation may need to cover a larger time frame. Hence, the temporal resolution is reduced. However, since the breathing state is expected to be mostly constant during this time, motion artifacts can be expected not to occur, due to only very little respiratory motion in this time frame.

According to an embodiment, the X-ray dose is modulated such that the X-ray dose is zero when the redundancy modulation is applied. For example, an X-ray source may be switched off or blocked. Advantageously, this embodiment may reduce the applied X-ray dose even further. Reconstruction bins located within this period may be shifted towards exhalation or inhalation.

The embodiments described herein may be combined with each other unless indicated otherwise. For example, several or all of the necessary conditions may be applied at the same time and/or the application of at least one or several of the necessary conditions may be combined with an embodiment for estimating the end of the data-redundant breathing phase.

According to one or more example embodiments, a computer program comprising instructions which, when the program is executed by a control unit of a computed tomography system, cause the computed tomography system to carry out the method as described herein, is provided. All features and advantages of the method may be adapted to the computer program and vice versa.

According to one or more example embodiments, a computer-readable storage medium, in particular non-transient storage medium is provided. The computer-readable storage medium comprises instructions which, when executed by a control unit of a computed tomography system, cause the computed tomography system to carry out the method as described herein. All features and advantages of the method and of the computer program may be adapted to the computer-readable storage medium and vice versa.

According to one or more example embodiments, a computed tomography system is provided. The computed tomography system comprises a monitoring sensor for monitoring a respiratory signal of a subject, wherein the system is configured to carry out the method as described herein. All features and advantages of the method, of the computer program, and of the computer-readable storage medium may be adapted to the computed tomography system and vice versa. For example, the monitoring sensor may be a strain gauge and or a belt with a strain gauge, in particular as described herein. Additionally or alternatively, the monitoring sensor may be a camera that works together with a light marker as described herein. For example, the computed tomography system may comprise a processing unit that is configured to control and initiate the method steps.

FIG. 1 shows a flow diagram of a computer-implemented method for reducing an X-ray dose applied on a subject during a respiration-correlated computed tomography scan according to an embodiment of the invention. In a first step 101, during a beam-on period of the scan, the beginning of a data-redundant breathing phase is determined. For this purpose, a respiratory signal is monitored that can be used to determine the beginning of the data-redundant breathing phase. For example, the respiratory signal may be monitored via an infrared marker 2 being placed on the chest of the subject 5 and a corresponding infrared camera 1. However, the respiratory signal may also be monitored differently e.g. via a strain gauge placed around the subject's 5 chest. The respiratory signal may be a signal that is monitored anyway for the purpose of the respiration-correlated computed tomography scan. For example, a breathing phase may be determined to be data-redundant when it is estimated to provide no significant additional breathing states during the current breathing cycle and/or at the current couch position. This may be done via conditions such as a change of the breathing state over time being estimated to be below a threshold and/or a variance of the breathing state being estimated to remain within a predetermined range. Examples of conditions based on which a data-redundant breathing phase may be determined are given in FIGS. 3 and 4. In a further step 102, during the data-redundant breathing phase, a redundancy modulation is applied to the applied X-ray dose such that the X-ray dose is reduced during the data-redundant breathing phase. The X-ray dose may be modulated by reducing an X-ray tube current when the redundancy modulation is applied. Optionally, the X-ray tube current may be reduced to zero or the X-ray beam may be block such that the X-ray dose applied to the subject 5 is zero when the redundancy modulation is applied. In a further step 103, the end of the data-redundant breathing phase is determined. For this purpose, the monitored respiratory signal may also be used in order to determine the end of the data-redundant breathing phase. In a further step 104, at the end of the data-redundant breathing phase as determined, the scan is continued without the redundancy modulation of the X-ray dose, i.e. by applying the normal X-ray dose.

Figure 2:
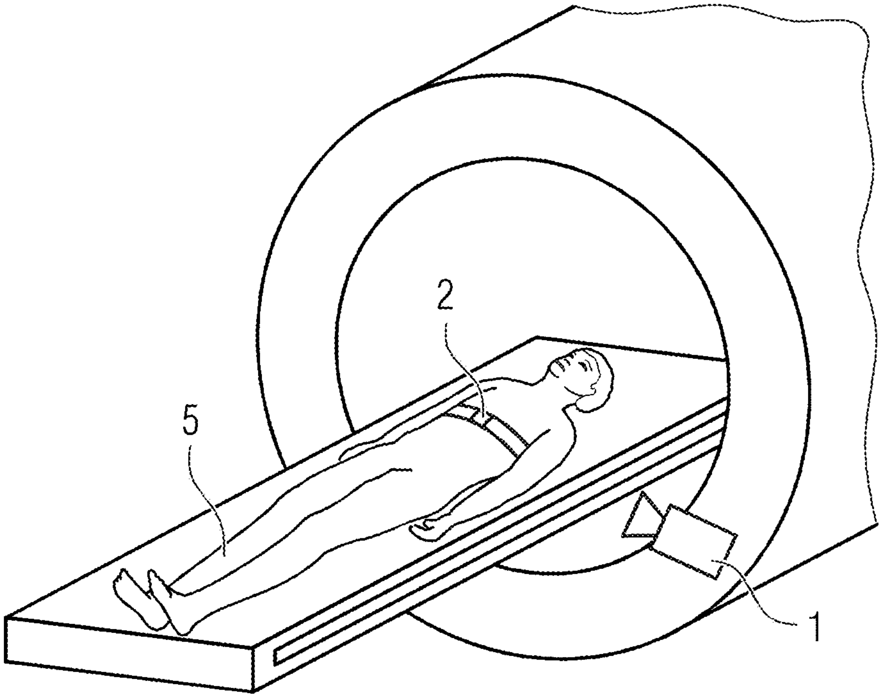
FIG. 2 shows a computed tomography system according to an embodiment of the invention.

FIG. 2 shows a computed tomography system according to an embodiment of the invention. The system is configured to carry out the method as described with respect to FIG. 1. The Computed tomography system comprises a monitoring sensor 1 for monitoring a respiratory signal of a subject 5. In this embodiment, the monitoring sensor 1 is an infrared camera 1 that works together with an infrared marker 2 on the subject's 5 chest.

Figure 3:
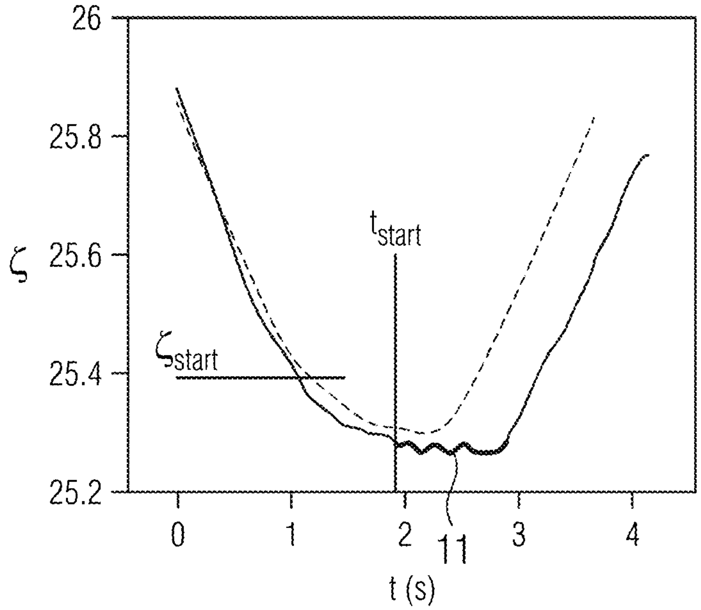
FIG. 3 is a graph of an exemplary respiratory signal, namely a chest elevation in cm, over the time of one breathing cycle.
Figure 4:
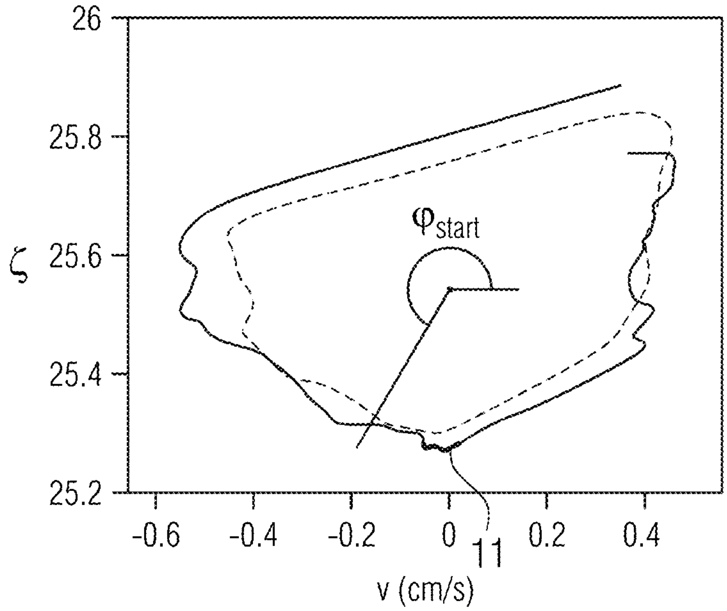
FIG. 4 is a graph of an exemplary respiratory signal, namely a chest elevation in cm, versus the breathing velocity.
Figure 5:
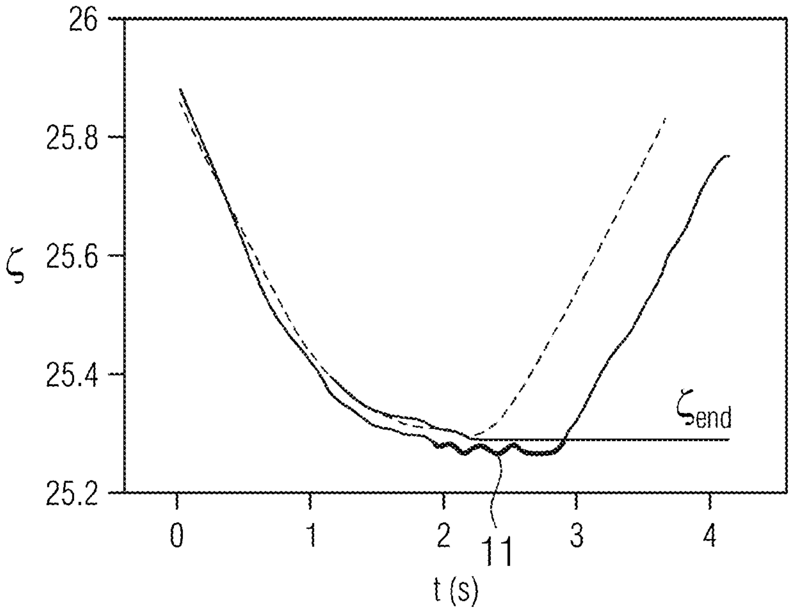
FIG. 5 is a graph of an exemplary respiratory signal, namely a chest elevation in cm, over the time of one breathing cycle.

FIGS. 3 to 5 illustrate an exemplary breathing cycle and the application of conditions for determining the beginning (FIGS. 3 and 4) and end (FIG. 5) of a data-redundant breathing phase. On the vertical axis of the plots the respiratory signal is plotted, which is a c. The absolute values given here are arbitrary based on the monitoring setup. Relevant are the relevant values between the different breathing states. The horizontal axis of FIGS. 3 and 5 shows the time in seconds. The horizontal axis of FIG. 4 shows the breathing velocity in cm/s. Generally, the respiratory signal (also referred to as breathing state or breathing signal), corresponding to an elevation of a subject's 5 chest, is denoted as $\zeta_i$, wherein i denotes a point in time. The derivative of the respiratory signal (also referred to as breathing velocity) at time point i is denoted as $\dot{\zeta}_i$. The respiratory signal $\zeta_i$ (FIGS. 3 and 5) and the breathing velocity $\dot{\zeta}_i$ (FIG. 4) are shown as continuous line. Based on the monitored respiratory signal, a reference breathing signal is denoted $\zeta^{ref}$. The reference breathing signal $\zeta^{ref}$ is shown as dashed line.

In this embodiment, there are three necessary conditions for the determination of the beginning of a data-redundant breathing phase. These conditions are a time criterion (tstart, see FIG. 3), an amplitude criterion (ζstart, see FIG. 3), and a phase criterion (φstart, see FIG. 4). Furthermore, there is an end criterion (ζend, see FIG. 5) that determines the end of the data-redundant breathing phase.

The time criterion is defined by the term $$\exists\, \zeta_i:\ \sum_{j=i_{100\%}}^{i} H(\zeta_{j-1}-\zeta_j) \geq 1.1 \times i_{5\%exh}^{ref},$$

wherein $i_{100\%}$ is the sample index representing the last state of maximal inhalation (i.e., the beginning of the current breathing cycle), H(x) is the Heaviside step function, $$i_{5\%exh}^{ref}$$

is the sample index corresponding to the 5% exhalation state, i.e. 5% above the minimum breathing state, in the reference breathing cycle. This time criterion is marked in FIG. 3 with a vertical line that is named "tstart". The time criterion is fulfilled as soon as the time (tracked on the horizontal axis) is beyond this line.

The amplitude criterion is defined by the term $$\exists\, \zeta_i:\ \zeta_i \leq \mathrm{median}(\zeta_{100\%}) - 0.8 \times \Delta\zeta^{ref}$$

wherein median($\zeta_{100\%}$) is the median of all previous samples that represent measurements at end-inhalation, and $\Delta\zeta^{ref}$ is the peak-to-peak amplitude of the reference breathing cycle. This amplitude criterion is marked in FIG. 3 with a horizontal line that is named "ζstart". The amplitude criterion is fulfilled as soon as the respiratory signal ζ drops below this line.

The phase criterion is defined by the term $$\exists\, \zeta_i:\ \varphi_i \geq \varphi_{5\%exh}^{ref},$$

wherein the phase is defined as the polar angle $\varphi_i$ of the point ($\dot{\zeta}_i$, $\zeta_i$) with respect to the centre of mass of the reference breathing cycle. Hence, the phase of at least one measurement must have been greater than or equal to the phase at 5% exhalation state in the reference breathing cycle. This phase criterion is marked in FIG. 4 with an angle line that is named "φstart" and that has its origin in the centre of mass of the reference breathing cycle (dashed line). The phase criterion is fulfilled as soon as the angle of the point ($\dot{\zeta}_i$, $\zeta_i$), that moves counter-clockwise, crosses this angle line.

If at any point in time each of the three criteria has been fulfilled during at least one previous (or the current) measurement sample during the current breathing cycle, the redundancy modulation is applied. The duration of the redundancy modulation is marked 11. In this example, the critical criterion, i.e. the criterion fulfilled last, is the time criterion (ζstart). However, this may differ depending on properties of the individual subject's 5 breathing cycle.

The redundancy modulation is stopped as soon as the end criterion is fulfilled. Namely the data-redundant breathing phase and thus the redundancy modulation ends as soon as the breathing signal exceeds a certain margin above the minimal breathing signal of the current cycle. In FIG. 5 it can be seen that the minimum breathing signal and thus the end criterion (ζend) changes with time during the exhalation phase and is mostly constant during the data redundant breathing phase. When inhalation begins (i.e. the respiratory signal exhibits an incline) the end criterion also remains constant. The incline of the respiratory signal triggers the end criterion ζend and, thus, the end of the redundancy modulation.

Figure 6:
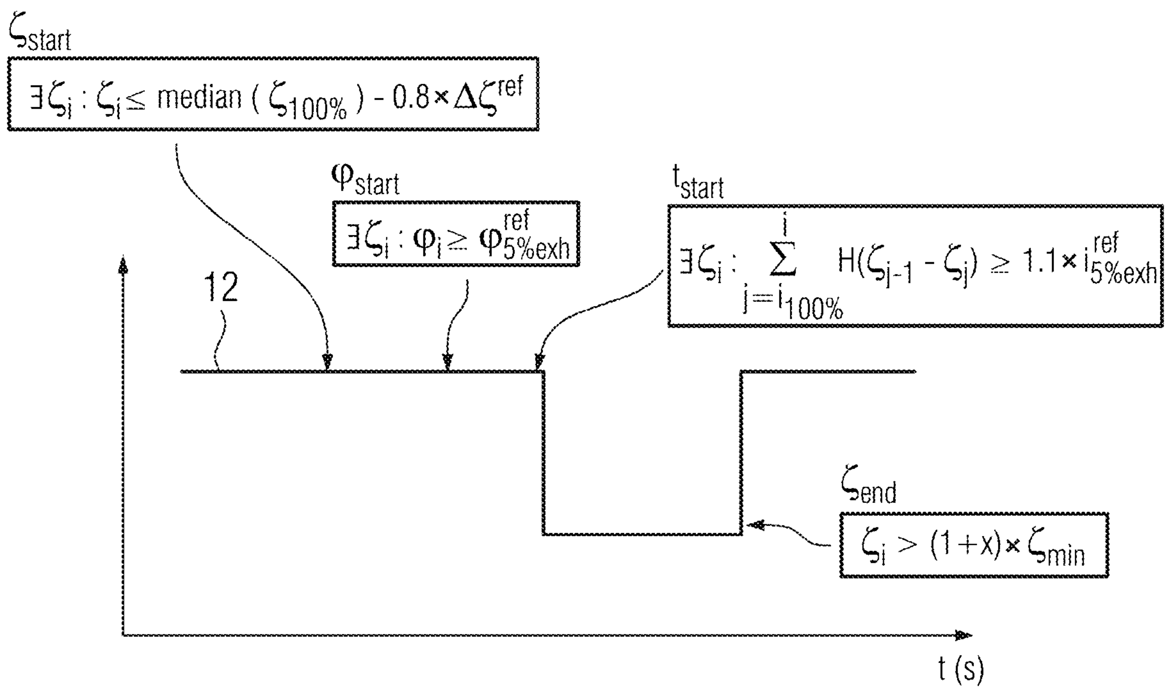
FIG. 6 is a graph of X-ray dose over time.

FIG. 6 illustrates a rough representation of the amount 12 of the X-ray dose that is applied before, during, and after a data-redundant breathing phase. At first a normal, i.e. higher X-ray dose is applied. Then, consecutively, the amplitude criterion (ζstart), the phase criterion (φstart), and the time criterion (tstart) are fulfilled. As soon as all three criteria (tstart being the last) are fulfilled, the redundancy modulation is applied by reducing the X-ray dose. As soon as the end criterion (ζend) is fulfilled, the redundancy modulation is stopped, and the original X-ray dose is applied again.

Figure 7:
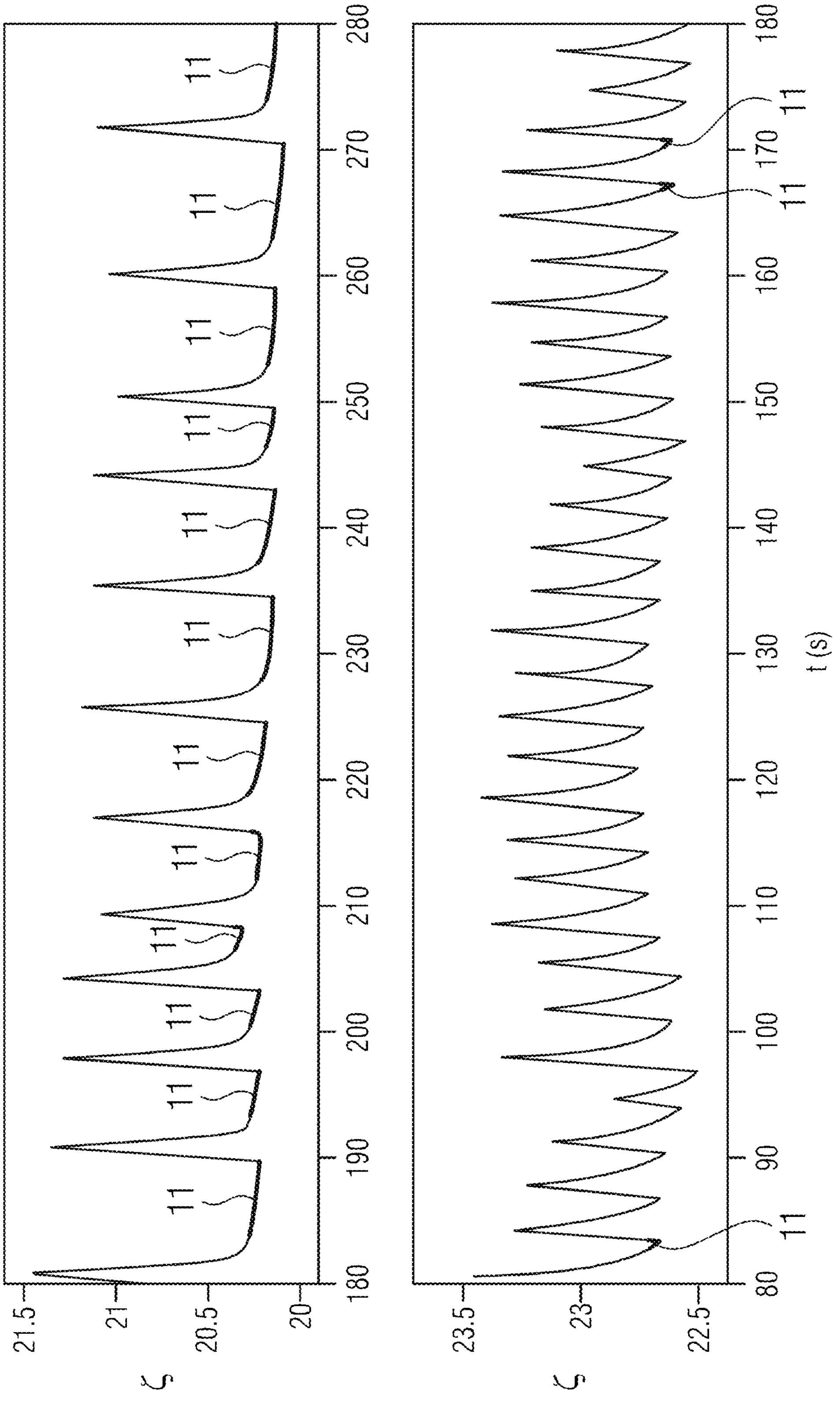
FIG. 7 shows two examples of respiratory signals plotted over multiple breathing cycles.

FIG. 7 shows two examples of respiratory signals plotted over multiple breathing cycles. The vertical axis represents the respiratory signal ζ and the horizontal axis represents the time t (in seconds). In the upper example there are long breathing pauses that occur after each exhalation. Correspondingly there are long data-redundant phases (marked with markings 11) during which the redundancy modulation is applied. Thus, in this upper example, a considerable amount of X-ray dose can be reduced. Up to 50% of the X-ray dose applied to the patient may be saved without reducing data completeness to reconstruct a full 4D-CT data set. In the lower example, there are only a few short breathing pauses that occur after each exhalation. Correspondingly there are only a few short data-redundant phases (marked with markings 11) during which the redundancy modulation is applied. In this lower example, only little X-ray dose may be saved.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, or instructions, some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, combination with additional in microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

The invention claimed is:

1. A computer-implemented method for reducing an X-ray dose applied on a subject during a respiration-correlated computed tomography scan, the method comprising:

determining a beginning of a data-redundant breathing phase during a beam-on period of the respiration-correlated computed tomography scan;

applying a redundancy modulation to the X-ray dose such that the X-ray dose is reduced during the data-redundant breathing phase;

determining an end of the data-redundant breathing phase; and continuing the respiration-correlated computed tomography scan without the redundancy modulation of the X-ray dose at the end of the data-redundant breathing phase, wherein a phase space is defined by a coordinate system having a first axis being a breathing state and a second axis being a time-dependent change of the breathing state, a current polar angle of a point in the phase space at a current breathing state and a current time-dependent derivative of the breathing state is defined with respect to a center of mass of a reference breathing cycle in the phase space, and the determining the beginning of the data-redundant breathing phase is based on the current polar angle being greater than or equal to a reference angle, the reference angle being based on the reference breathing cycle.

2. The method of claim 1, further comprising:

determining a breathing phase to be data-redundant based on estimating the breathing phase to provide no significant additional breathing states at least one of during a current breathing cycle or at a current couch position.

3. The method of claim 1, further comprising:

determining a breathing phase to be data-redundant based on at least one of, estimating a change of a breathing state over time to be below a threshold, or estimating a variance of the breathing state to remain within a range.

4. The method of claim 1, wherein the determining the beginning of the data-redundant breathing phase is based on a signal length since a last end-inhalation state having a defined minimum length relative to a reference exhalation duration.

5. The method of claim 1, wherein the determining the beginning of the data-redundant breathing phase is based on a current breathing cycle having gone through a minimum fraction of a reference breathing amplitude during exhalation since a last end-inhalation state.

6. The method of claim 1, wherein the determining the beginning of the data-redundant breathing phase is based on a current time-dependent change of a breathing state being low.

7. The method of claim 1, wherein the determining the end of the data-redundant breathing phase includes estimating the end of the data-redundant breathing phase to be reached based on at least one of, a current breathing state exceeding a first minimal threshold, or a change of the current breathing state exceeding a second minimal threshold.

8. The method of claim 1, wherein the determining the end of the data-redundant breathing phase includes estimating the end of the data-redundant breathing phase to be reached based on the current breathing state exceeding a defined margin above a minimal breathing state recorded at least one of, in a current breathing cycle, in a current couch position, or since a last end-inhalation state.

9. The method of claim 1, further comprising:

modulating the X-ray dose by reducing an X-ray tube current based on the redundancy modulation being applied.

10. The method of claim 1, further comprising:

modulating the X-ray dose such that the X-ray dose is zero based on the redundancy modulation being applied.

11. The method of claim 1, wherein the determining the beginning of the data-redundant breathing phase and the determining the end of the data-redundant breathing phase include monitoring a respiratory signal.

12. A non-transitory computer program product comprising instructions which, when executed by a control unit of a computed tomography system, cause the computed tomography system to perform the method of claim 1.

13. A non-transitory computer-readable storage medium comprising instructions which, when executed by a control unit of a computed tomography system, cause the computed tomography system to perform the method of claim 1.

14. A computed tomography system comprising:

a monitoring sensor configured to monitor a respiratory signal of a subject, wherein the system is configured to perform the method of claim 1.

15. The method of claim 2, further comprising:

determining a breathing phase to be data-redundant based on at least one of, estimating a change of a breathing state over time to be below a threshold, or estimating a variance of the breathing state to remain within a range.

16. The method of claim 15, wherein the determining the beginning of the data-redundant breathing phase is based on a signal length since a last end-inhalation state having a defined minimum length relative to a reference exhalation duration.

17. The method of claim 16, wherein the determining the beginning of the data-redundant breathing phase is based on the current breathing cycle having gone through a minimum fraction of a reference breathing amplitude during exhalation since the last end-inhalation state.

18. The method of claim 17, wherein the determining the beginning of the data-redundant breathing phase is based on a current time-dependent change of the breathing state being low.

19. The method of claim 18, wherein the determining the end of the data-redundant breathing phase includes estimating the end of the data-redundant breathing phase to be reached based on at least one of, a current breathing state exceeding a first minimal threshold, or a change of the current breathing state exceeding a second minimal threshold.

20. The method of claim 18, wherein the determining the end of the data-redundant breathing phase includes estimating the end of the data-redundant breathing phase to be reached based on the current breathing state exceeding a defined margin above a minimal breathing state recorded at least one of, in the current breathing cycle, in the current couch position, or since the last end-inhalation state.

* * * * *